Patent Number: 4,948,878
Date of Patent: Aug. 14, 1990

[54] PROCESS AND APPARATUS FOR PRODUCING METAL ALKOXIDES

[75] Inventors: Dorothy E. Lozowski, Hastings-on-Hudson; Donald D. Schaller, S. Monsey, both of N.Y.

[73] Assignee: Akzo America Inc., New York, N.Y.

[21] Appl. No.: 324,973

[22] Filed: Mar. 20, 1989

Related U.S. Application Data

[63] Continuation of Ser. No. 39,255, Apr. 17, 1987, abandoned.

[51] Int. Cl.⁵ .............................................. C07C 29/70
[52] U.S. Cl. ..................................... 534/15; 502/178; 568/678
[58] Field of Search ................... 534/15; 556/1, 7, 27, 556/42, 45, 51, 54, 57, 113, 130, 136, 146, 182, 188

[56]      References Cited
       U.S. PATENT DOCUMENTS

| | | | |
|---|---|---|---|
| 2,965,663 | 12/1960 | Smith et al. | 556/182 |
| 3,094,546 | 6/1963 | Towers | 556/182 |
| 3,278,571 | 10/1966 | Mazdiyasni et al. | 534/15 |
| 3,757,412 | 9/1973 | Mazdiyasni et al. | 534/15 |
| 4,590,289 | 5/1986 | Albert et al. | 556/188 |
| 4,670,573 | 6/1987 | Greco et al. | 556/182 |

*Primary Examiner*—Matthew A. Thexton
*Assistant Examiner*—John M. Covert
*Attorney, Agent, or Firm*—Richard P. Fennelly; Louis A. Morris

[57]              ABSTRACT

The yield of metal alkoxides formed by refluxing an alcohol-containing liquid, also containing catalyst, from a reactor vessel into a reflux column containing reactive metal is provided. The yield of the desired alkoxide is increased by withdrawing a portion of the alcohol reactant and catalyst from the reactor and introducing them into the column above the position occupied by at least a portion of the metal. The thus introduced catalyst-containing alcohol reactant makes contact with the metal and thereby increases the yield of metal alkoxide as it is allowed to flow back into the reactor vessel.

5 Claims, 1 Drawing Sheet

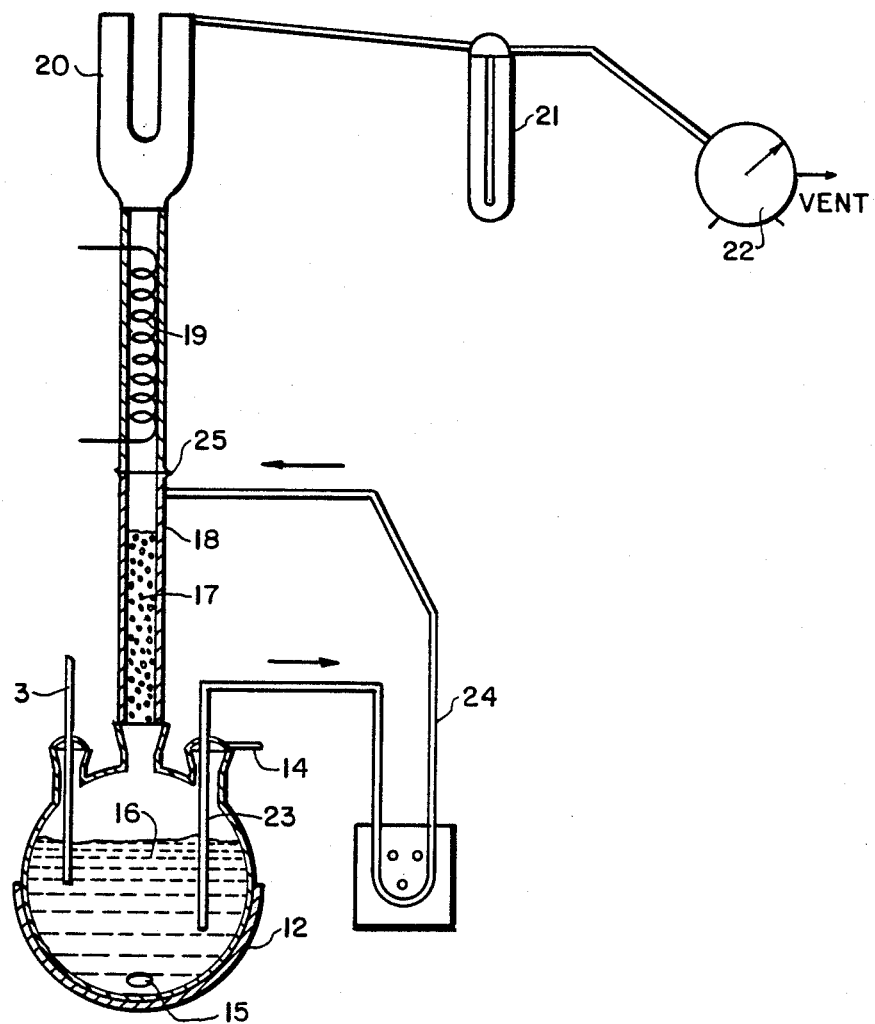

PROCESS AND APPARATUS FOR PRODUCING METAL ALKOXIDES

This is a continuation of application Ser. No. 07/039,255 filed Apr. 17, 1987 now abandoned.

BACKGROUND OF THE INVENTION

1. Field of the Present Invention

The present invention relates to a process and apparatus for making metal alkoxides by the reaction of a metal and alcohol wherein the metal is suspended in a column above a reactor vessel containing alcohol. The alcohol is refluxed so that it makes contact with the metal in the column.

2. Description of the Prior Art

U.S. Pat. No. 2,965,663 to W. E. Smith et al. shows the general technique of making metal alkoxides by using the general type of process and apparatus shown herein. The Smith et al. patent illustrates a reactor containing alcohol which has on its upper surface a column containing the reactive metal. The alcohol is heated so that it refluxes and makes contact with the metal in the column. The alkoxide product drips back into the reactor after the alcohol has made contact with the metal in the column. Provision is made for removal of the product from the reactor with recycle of reactant alcohol to the reactor. An improved version of this general procedure is shown in U.S. Pat. No. 3,094,546 to R. S. Towers which provide for a by-pass line allowing for by-passing of a certain portion of the alcohol reagent from the column directly into the reactor without making contact with the reactant metal.

Some metals react slowly or do not react at all with alcohols to form the respective alkoxides without the use of a catalyst. For example, U.S. Pat. No. 3,278,571 to K. S. Mazdiyasni et al. teaches the use of certain mercuric chloride catalysts to form certain alkoxides of yttrium, dysprosium, and ytterbium. When less reactive metal/alcohol combinations are proposed for use in the general type of column/reactor procedure and apparatus shown in the aforementioned Smith et al. and Towers patents, the reaction may proceed very slowly or not at all. Therefore, a need exists for a modified version of the aforementioned column/reactor apparatus to initiate and sustain the reaction when such sluggish or non-reactive metal/alcohol combinations are employed. It is to this need that the present process and apparatus are directed.

SUMMARY OF THE PRESENT INVENTION

The present invention involves the reaction of metal and alcohol by suspending the reactive metal in a column above a reactor vessel containing the alcohol, and solvent, if desired, and refluxing the alcohol so that it contacts the metal in the column. A catalyst can be introduced either directly into the reactor vessel or with the metal in the column. The present process is specifically directed to withdrawing a portion of the alcohol reagent from the reactor and introducing it into the column above the position occupied by at least a portion of the metal so that the metal is contacted by both the alcohol and catalyst. Contact with the catalyst can initiate the reaction and increase the yield of metal alkoxide flowing back into the reactor vessel.

DESCRIPTION OF THE DRAWING

The present invention will be more fully understood by reference to the Drawing which forms a portion of the present specification wherein the FIGURE represents a view from the side, in cross section, of a suitable laboratory scale apparatus for use in conjunction with the present process.

DETAILED DESCRIPTION OF THE PRESENT INVENTION

The Drawing illustrates a suitable laboratory apparatus for preparing metal alkoxides in conjunction with the present invention which has been found to be suitable for use. It comprises a suitable reactor vessel equipped with a heating mantle 12 and thermometer 3. A nitrogen feed tube 14 is provided for the appropriate purging of the apparatus with nitrogen. A stir bar 15 is provided to allow for stirring of the liquid 16 which is in the reactor. This liquid initially comprises alcohol and a solvent, if desired, and, as the reaction proceeds, will comprise alcohol, catalyst and a mixture of alkoxide product. A suitable catalyst can be added either to the liquid 16 or with metal reactant 17. The metal reactant 17 is placed in the column 18 attached to an opening in the reactor. A condenser 19, cold finger tube 20, cold trap 21, and wet test meter 22 are also provided.

The types of metal reactant 17 which can be used in conjunction with the present invention include those metals which are reactive with alcohols to form metal alkoxides. Included within this category are such reactive metals as sodium, magnesium, aluminum, lithium, and calcium. Also included are the less reactive metals which require a catalyst. Included are such transition and rare earth metals as yttrium, dysprosium, and ytterbium. Generally speaking, the type of alcohol that can be used in the process includes straight or branched chain alcohols or glycol ethers. Representative organic moieties in the alcohols or ethers include the $C_1-C_4$ alkyl groups. For purposes of the present invention, the term "alcohol" is meant to encompass the use of glycol ether reactants which are reactive by virtue of alcohol functionality in their molecule. Representative catalysts that can be used include mercuric chloride as well as others that are known to persons of ordinary skill in the art.

In accordance with the present invention, a portion of the alcohol-containing liquid in the reactor is removed therefrom and is fed back to the column holding the metal reactant such that it is introduced at a position on the column above at least a portion of the metal. As it is allowed to flow back over the metal from its point of entry into the column, it ensures a further contacting of the metal with the catalyst and alcohol. This contact between the catalyst and metal can initiate a reaction where one would not occur without a catalyst, or it can reduce the induction period required for the reaction to start. The enhanced contact between the alcohol and metal can further clean the metal surface of the product, and it can allow a sustained reaction at temperatures below the boiling point of the alcohol if lower temperatures are desired.

In the Drawing which forms a portion of the present specification, a dip tube 23 is provided which extends into liquid 16 containing the alcohol reactant. The dip tube is attached at its upper end to conduit 24 which passes through a pump (MASTERFLEX brand) which acts to remove a portion of the liquid 16 from the reactor as shown by the arrows with its introduction into the column at 25 which is located preferably above a substantial portion of the metal reactant 17. This allows for further contacting of the alcohol reactant and catalyst with the metal and will increase the yield of desired alkoxide product, especially in those cases in which the metal/alcohol combination is rather sluggish and needs to be promoted by the presence of a suitable catalyst.

The present invention is further illustrated by the Example which follows.

EXAMPLE

Yttrium metal turnings (23 grams) intermixed with ceramic saddles were added to a 1-inch diameter glass column above a 1-liter flask. The saddles were added to increase the void space in the column to avoid flooding. To the flask were added 820 milliliters of isopropanol which had been dried with molecular sieves, and 0.60 grams of mercuric chloride. A MASTERFLEX pump was used to circulate the alcohol and catalyst over the metal as shown in the Drawing. The flask contents were heated to boiling (~82° C.). After approximately 3 hours 20 minutes, bubbles were seen evolving from the surface of the yttrium turnings, indicating hydrogen evolution, and thereby reaction. After about 5 hours total reflux time, it was noted that the liquid in the reaction flask had turned metallic grey, as a further indication of reaction. The system was cooled overnight and heated again the next morning. After another hour of reflux and recirculation, the pump was turned off, and the reaction was sustained by reflux alone. Reflux was maintained for an additional 5 hours with the pump turned on again only briefly.

At the end of the reaction the solution was stripped by distillation to remove excess isopropanol, and 500 milliliters of toluene were added to solubilize the product, yttrium isopropoxide. The solution was filtered through filter aid. A total of 362 grams of a clear, slightly brownish liquid was obtained. This material was analyzed as 3.1 weight percent yttrium, indicating that 33.6 grams of yttrium isopropoxide had been prepared.

The foregoing Example should not be construed in a limiting sense since it is provided to merely illustrate certain preferred embodiments of the present invention. The scope of protection that is sought is set forth in the claims which follow.

We claim:

1. An improved process for preparing metal alkoxides which comprises:
   (a) suspending a reactive transition metal in a column above a reactor vessel containing alcohol and catalyst;
   (b) refluxing the alcohol so that it contacts the metal in the column; and
   (c) also withdrawing a portion of the alcohol and catalyst from the reactor and introducing it, as a liquid into the column above the position of at least a portion of the metal so that the alcohol and catalyst contacts the metal and thereby increases the yield of metal alkoxide as it flows back into the reactor vessel.

2. A process as claimed in claim 1 wherein the alcohol comprises a $C_1$-$C_4$ alkyl group.

3. A process as claimed in claim 1 wherein the metal is a rare earth metal.

4. A process as claimed in claim 1 wherein the metal is selected from the group consisting of yttrium, dysprosium, and ytterbium.

5. A process as claimed in claim 2 wherein the metal is selected from the group consisting of yttrium, dysprosium, and ytterbium.

* * * * *